United States Patent
Hassan et al.

(10) Patent No.: US 8,026,402 B2
(45) Date of Patent: Sep. 27, 2011

(54) HIGH SHEAR PROCESS FOR CYCLOHEXANE PRODUCTION

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation

( * ) Notice: Subject to any disclaimer, the term of this patent is extended or adjusted under 35 U.S.C. 154(b) by 565 days.

(21) Appl. No.: 12/138,276

(22) Filed: Jun. 12, 2008

(65) Prior Publication Data

US 2009/0005621 A1    Jan. 1, 2009

Related U.S. Application Data

(60) Provisional application No. 60/946,533, filed on Jun. 27, 2007.

(51) Int. Cl.
*C07C 5/10* (2006.01)

(52) U.S. Cl. ........ 585/270; 585/266; 585/275; 585/276; 585/277; 261/83; 366/241; 366/293; 366/294; 366/295; 366/316

(58) Field of Classification Search ............. 585/266, 585/269–270, 275–277; 366/101–105, 241, 366/293–295, 316; 261/83
See application file for complete search history.

(56) References Cited

U.S. PATENT DOCUMENTS

| | | | |
|---|---|---|---|
| 3,781,320 A | 12/1973 | Irwin | |
| 5,856,603 A * | 1/1999 | Rekker et al. | 585/270 |
| 5,877,350 A | 3/1999 | Langer et al. | |
| 6,187,980 B1 | 2/2001 | Gildert | |
| 6,368,366 B1 | 4/2002 | Langer et al. | |
| 6,368,367 B1 | 4/2002 | Langer et al. | |
| 6,383,237 B1 | 5/2002 | Langer et al. | |
| 2003/0043690 A1 | 3/2003 | Holl | |
| 2004/0052158 A1 | 3/2004 | Holl | |
| 2005/0033069 A1 | 2/2005 | Holl et al. | |

FOREIGN PATENT DOCUMENTS

EP    1604969 A1    12/2005

OTHER PUBLICATIONS

Tsuji T. et al. (2005). Fluid Phase Equilibria, 228-229, 499-503.*
International Search Report, International Application No. PCT/US2008/067243, dated Feb. 19, 2009.

* cited by examiner

*Primary Examiner* — Robert J Hill, Jr.
*Assistant Examiner* — Brian A. McCaig
(74) *Attorney, Agent, or Firm* — Porter Hedges LLP; Timothy S. Westby

(57) ABSTRACT

A high shear mechanical device incorporated into a process and system for the production of cyclohexane is capable of decreasing mass transfer limitations, thereby enhancing the cyclohexane production process. A system for the production of cyclohexane from benzene and hydrogen, the system comprising a reactor, solid catalyst, and a high shear device, the outlet of which is fluidly connected to the inlet of the reactor; the high shear device capable of providing an emulsion of hydrogen gas bubbles within a liquid comprising benzene, the bubbles having an average bubble diameter of less than about 100 μm.

24 Claims, 2 Drawing Sheets

HIGH SHEAR PROCESS FOR CYCLOHEXANE PRODUCTION

CROSS-REFERENCE TO RELATED APPLICATIONS

This application claims the benefit under 35 U.S.C. §119 (e) of U.S. Provisional Patent Application No. 60/946,533 filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the hydrogenation of aromatic hydrocarbons, and more particularly to apparatus and methods for heterogeneous catalytic hydrogenation of aromatic hydrocarbons. More specifically, the disclosure relates to the reduction of mass transfer limitations of such methods in the apparatus and methods of hydrogenating 2. Background of the Invention Heterogeneous catalytic hydrogenation processes of various kinds are widely practiced on a commercial scale. Typical hydrogenation reactions are conducted at a pressure of from about 1 bar (100 kPa) to about 300 bar (30,000 kPa) and a temperature within the range of from about 40° C. to about 350° C. Examples include hydrogenation of aldehydes to alcohols and the hydrogenation of unsaturated hydrocarbons to saturated hydrocarbons.

Catalytic hydrogenation is in all the above cases a heterogeneous process. In designing a hydrogenation plant a chemical engineer has to decide whether the process is to be operated as a liquid phase process or as a vapor phase process. The former offers the possibility of a compact plant but often high operating pressures have to be used as a rate determining factor is usually the low solubility of hydrogen in the organic liquid phase. This means that the costs of plant construction and operation are significant factors in the overall process economics.

An example of hydrogenation of an unsaturated hydrocarbon is the production of cyclohexane from benzene. Cyclohexane is a cycloalkane with the molecular formula $C_6H_{12}$. Cyclohexane is used as a nonpolar solvent for the chemical industry and as a raw material for the industrial production of caprolactam and adipic acid, both of which are intermediates used in the production of nylon. On an industrial scale, cyclohexane is produced by reacting benzene with hydrogen. Typical catalysts for such hydrogenation reactions include Group VIII metal catalysts, such as nickel, palladium and platinum. This reaction is exothermic. The use of high temperatures is normally recommended so as to maximize conversion of benzene to cyclohexane, but isomerization of cyclohexane to methyl cyclopentane, which is extremely difficult to separate from cyclohexane, can occur.

Over the years, researchers have developed numerous processes for manufacturing cyclohexane from the hydrogenation of benzene. The majority of these processes differ from each other in the techniques used to compensate for impurities, found in either the reaction components themselves or that are generated during the hydrogenation process.

For example, U.S. Pat. No. 3,711,566 (Estes et al.) describes a process in which aromatic hydrocarbon feedstock containing sulfur are hydrogenated using a fluoridated platinum catalyst. Sulfur, a known poison to platinum catalysts, causes rapid deactivation of the catalyst as the hydrogenation process proceeds. Adding fluorine to the catalyst reduces sulfur poisoning; however, this undesirably increases hydrocracking activity that also deactivates the catalyst. Estes et al. inhibited hydrocracking activity by adding extremely small amounts, of carbon monoxide (a poison of metal catalysts itself) to the pure-hydrogen feed stream. This allowed the carbon monoxide to interact with the acidity of the fluoridated catalyst surface and prevent reactions, like hydrocracking, from taking place. Because carbon monoxide can also poison and deactivate the catalyst, care must be exercised in both purifying the hydrogen feed stream and in adding the carbon monoxide to the pure-hydrogen feed stream in order to achieve proper hydrogenation. This type of hydrogenation process therefore appears most useful when the hydrocarbon feedstock contains substantial amounts of sulfur requiring the catalyst to contain fluorine to prevent the sulfur from poisoning the catalyst.

U.S. Pat. No. 4,626,604 (Hiles et al.) describes a process in which hydrogenation occurs in a series of catalytic stages using at least three adiabatic reaction vessels. Because hydrogenation occurs in stages, lower operating temperatures can be used, which in turn reduces the formation of byproducts such as esters that can poison the catalysts and decrease, catalytic activity. However, Hiles et al. requires that the liquid unsaturated aromatic hydrocarbon be vaporized prior to mixing with the hydrogen gas. Portions of the vaporized unsaturated aromatic hydrocarbon are then hydrogenated in each catalytic stage before the saturated hydrocarbon is cooled and condensed back to liquid-form.

Accordingly, there is a need in industry for improved systems and processes for hydrogenating liquid aromatic hydrocarbons, whereby effective conversion is obtained. For example, systems and processes for enhanced conversion of benzene to cyclohexane are desired; such systems desirably do not lead to formation of a significant amount of undesirable cracking products, such as methylcyclopentane.

SUMMARY OF THE INVENTION

A high shear system and method for accelerating liquid aromatic hydrocarbon hydrogenation is disclosed. The high shear system makes possible a reduction in mass transfer limitations, thereby increasing the reaction rate and enabling a reduction in reactor temperature, a reduction in reactor pressure, a reduction in contact time, and/or in increase in product yield. In accordance with certain embodiments of the present invention, a method is provided that makes possible an increase in the rate of an aromatic hydrogenation process by providing for more optimal time, temperature and pressure conditions than are currently used. The method employs a mechanical high shear device to provide improved time, temperature, and pressure conditions for accelerated chemical reactions between multi-phase reactants.

In an embodiment, the method comprises the use of a high shear device to provide for hydrogenation without the need for high volume, high pressure vessel reactors. Further, a method disclosed in an embodiment described herein comprises the use of a pressurized high shear device to provide for the production of cyclohexane without the need for high volume, high pressure vessel reactors.

These and other embodiments, features, and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
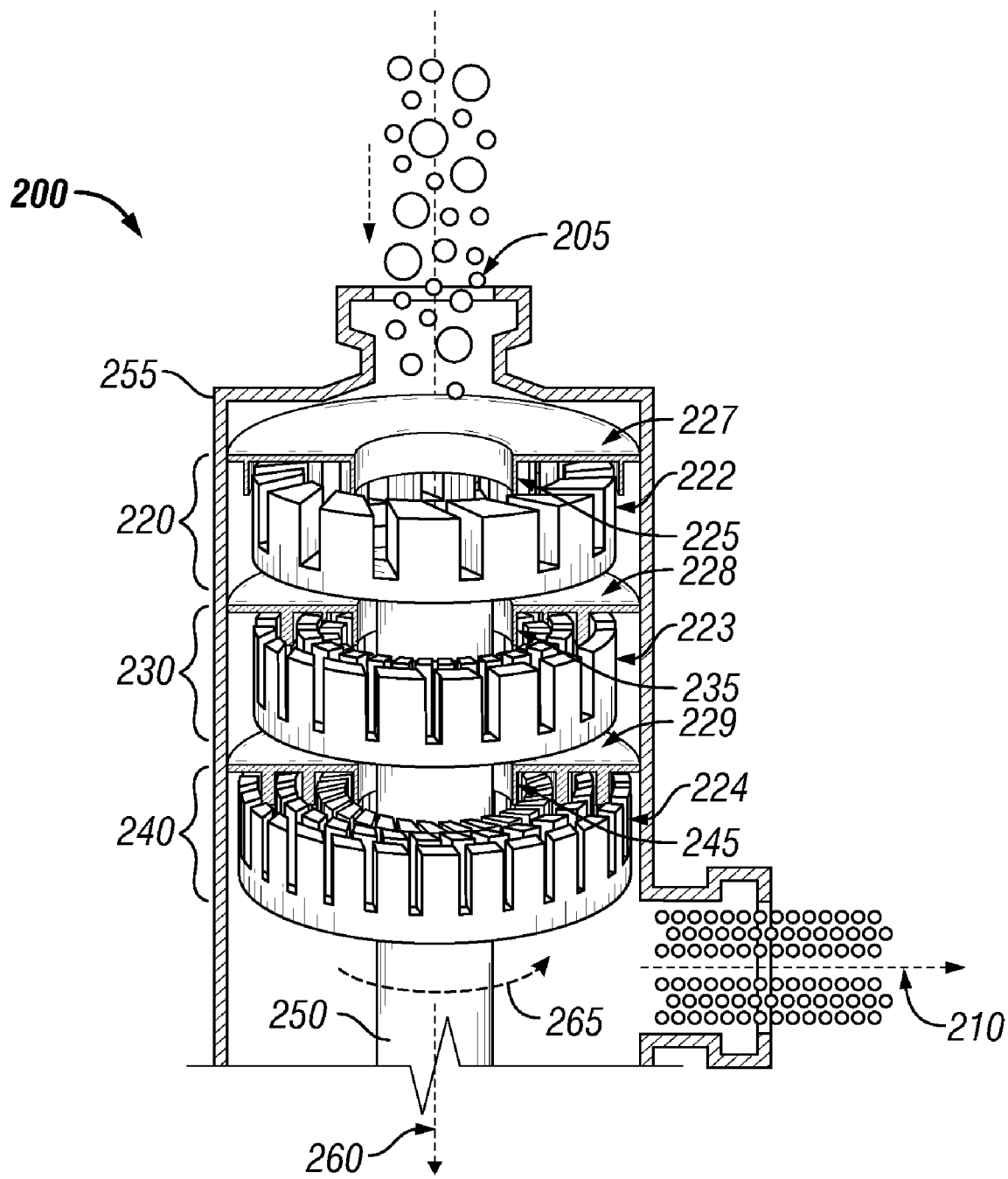
FIG. 1 is a cross-sectional diagram of a high shear device for the production of cyclohexane.

A hydrogenation system and method employs an external high shear mechanical device to provide rapid contact and mixing of chemical ingredients in a controlled environment in the reactor/mixer device. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants.

In conventional reactors, contact time for the reactants and/or catalyst is often controlled by mixing which provides contact with two or more reactants involved in a chemical reaction. A reactor assembly that comprises an external high shear mixer makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

High Shear Device

High shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 µm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule, or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The shear rate generated in a high shear device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec) $=\pi \cdot D \cdot n$, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, $2\pi R$, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate the hydrogen and benzene into free radicals, which then form into the corresponding cyclohexane product.

Figure 2:
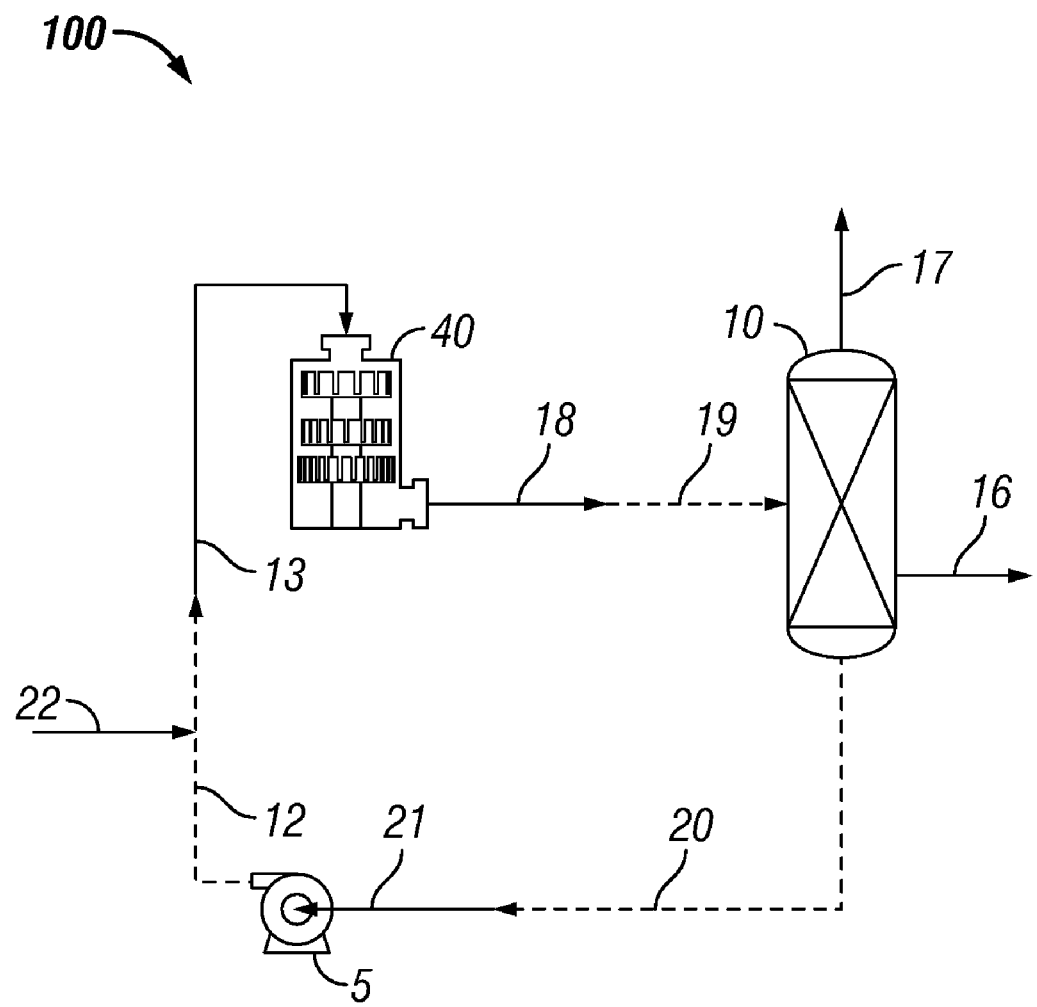
FIG. 2 is a process flow diagram according to an embodiment of the present disclosure for mediator-assisted high shear hydrogenation of liquid aromatic hydrocarbons.

Description of High Shear Process and System for Hydrogenation of Aromatic Hydrocarbon High shear system 100, hereinafter HSS 100, is suitable for the hydrogenation of liquid aromatic hydrocarbons. The process and system of the present disclosure will now be described in relation to a process and system for accelerating the rate of benzene hydrogenation. FIG. 2 is a schematic of a flow diagram of a benzene hydrogenation process employing a multi-phase reaction system and comprising a high shear device. As will be further discussed below, the disclosed process with high shear device reduces resistance to mass and heat transfer between multiple phases. FIG. 2 illustrates the basic components of a representative high shear multi-phase reaction system comprising pump 5, high shear device 40, and reactor 10.

Pump inlet stream 21 comprising benzene enters pump 5. The benzene in pump inlet stream 21 may be obtained from any source, including, but not limited to, hydrodealkylation, pyrolysis, catalytic reforming, or fractional distillation. Pump 5 is used to provide a controlled flow throughout high shear mixer 40 and high shear system 100. Pump 5 builds pressure and feeds external high shear device 40. In embodiments, pump 5 increases the pressure of pump inlet stream 21 to greater than about 203 kPa (about 2 atm) before pump exit stream 12. Alternatively, the pump 5 increased the pressure to at least about 2025 kPa (about 20 atm) before pump exit stream 12. The limiting factor being the pressure limitations of pump 5 and high shear device 40. The pressure may function to accelerate reaction rates in HSS 100.

In certain instances all contact parts of pump 5 are stainless steel. Alternatively it may be desirable to have, gold plated contact surfaces. Pump 5 may be any suitable pump, for example, a Roper Type 1 gear pump, Roper Pump Company (Commerce Georgia) or a Dayton Pressure Booster Pump Model 2P372E, Dayton Electric Co (Niles, Ill.).

Pump exit stream 12 is in fluid communication with HSD inlet stream 13. Pump exit stream 12 may undergo further processing prior to introduction to HSD 40. In certain instances dispersible reactant stream 22 is injected into inlet stream 13. Dispersible reactant stream 22 comprises 22 comprises hydrogen.

Of particular concern in a conventional hydrogenation of benzene process are impurities found in the hydrogen source and dispersible reactant stream 22, because such impurities often deactivate the catalyst used to promote the hydrogenation reaction. Carbon monoxide is one such impurity that can reversibly poison catalysts, like nickel, used in benzene hydrogenation processes. In the poisoning process, carbon monoxide is adsorbed onto the active sites of the nickel catalyst surface, thereby reducing the activity of the catalyst. Depending on the concentration of carbon monoxide in the hydrogen source, the nickel catalyst can rapidly deactivate.

In order to operate efficiently, most conventional benzene hydrogenation processes require that a highly pure hydrogen source be used. Relatively pure hydrogen sources for dispersible hydrogen stream 22 may be obtained, for example, from a steam reformer. Such hydrogen streams typically contain about 96 mole % hydrogen, about 4 mole % methane, and less than about 10 ppm of carbon monoxide and other impurities. Even with low carbon monoxide levels, hydrogen streams may be further purified to reduce the carbon monoxide levels to less than about 1 ppm before injection into high shear device inlet stream 13.

The hydrogen in dispersible reactant stream 22 may be obtained from a less pure source of hydrogen, for example from steam cracking, catalytic reforming, or hydroalkylation. Hydrogen streams obtained from these sources typically contain between about 10 mole % and about 80 mole % hydrogen. The remainder comprises impurities such as methane, other light hydrocarbons, and/or carbon monoxide. The level of carbon monoxide in hydrogen streams from these sources is often as great as about 5000 ppm, which prevents the use of these hydrogen sources in conventional benzene hydrogenation processes. U.S. Pat. No. 6,750,374, incorporated herein in by reference in its entirety, describes process for producing cyclohexane by benzene hydrogenation using an impure hydrogen source.

The HSD 40 is positioned in HSS 100 between pump 5 and reactor 10. HSD 40 comprises a mechanical device as described above. In certain instances HSS 100 may comprise a plurality of high shear devices 40. Multiple high shear devices 40 may be arranged in parallel, or in series as known to one skilled in the art. HSD 40 produces an emulsion of dispersible reactant stream 22 comprising hydrogen in benzene. High shear device exit stream 18 removes the emulsion from HSD 40. HSD exit stream 18 may be further processed or treated to remove impurities as known to one skilled in the art.

The HSD exit stream 18 is injected into reactor inlet stream 19. Reactor inlet stream 19 is in fluid communication with the reactor 10. Alternatively, high shear outlet stream 18 may directly enter reactor 10 without further processing, for example HSD exit stream 18 and reactor inlet stream 19 are the same stream. In certain embodiments, the reactor inlet stream 19 further comprises catalysts or reaction enhancers as known to one skilled in the art.

Reactor 10 is any type of reactor in which a multiphase reaction can propagate. In certain instances, the reactor 10 comprises a jacketed, stainless steel, tubular reactor. Further, the reactor 10 may comprise one or more tank or tubular reactors in series or in parallel. Generally, the pressure of reactor 10 is maintained above about 50 psig. Preferably, the pressure of reactor 10 is maintained at a pressure of from about 250 psig to about 2500 psig, and more preferably, a pressure of from about 400 psig to about 800 psig. During operation, the exotherm or hot spot temperature in reactor 10 is maintained above about 160° C., preferably from about 160° C. to about 340° C., and most preferably from about 190° to about 280° C. The reaction carried out by high shear process 100 in reactor 10 comprises a heterogeneous catalytic reaction involving a solid catalyst and at least one reactant in gas or liquid phase.

The catalysts used for the production of cyclohexane may be prepared according to any suitable technique known in the art. Typically, the catalyst comprises nickel and/or copper on an alumina or silica support. For example, U.S. Pat. No. 6,750,374 discloses catalyst comprising nickel and/or copper, said catalyst also optionally comprising chromium, manganese, iron, cobalt, zinc, molybdenum, tin, or combinations thereof. In embodiments, the catalyst comprises from about 15 wt % to about 35 wt % nickel, preferably from about 1 wt % to about 15 wt % copper, and most preferably from about 0 wt % to about 5 wt % chromium, manganese, iron, cobalt, zinc, molybdenum, tin, or mixtures thereof. In certain instances, the catalyst comprises from about 22 wt % to about 28 wt % nickel, from about 2 wt % to about 6 wt % copper, and from about 0 wt % to about 3 wt % chromium, manganese, iron, cobalt, zinc, molybdenum, tin, or combinations thereof. The support for the catalyst may comprise any suitable material known to those of skill in the art. In embodiments, the support comprises either alumina or silica.

In certain instances, an impure hydrogen feed may deactivate nickel catalysts. Once the nickel catalyst has deactivated, the catalyst may be regenerated by heating the catalyst at a temperature from about 220° C. to about 260° C. The temperatures required for catalyst regeneration tend to promote the formation of large quantities of undesirable cracking products if done in the presence of benzene or cyclohexane. In this instance, the reactor must be taken off-line before regeneration of the catalyst. As previously discussed herein, the processes to ensure a hydrogen feed free from contaminants may be undertaken as known to one skilled in the art.

Hydrogenation reactions may occur whenever suitable time temperature and pressure conditions exist. Hydrogenation may occur at any point in the flow diagram of FIG. 2 if temperature and pressure conditions are suitable. Where a slurry based catalyst is utilized, reaction is more likely to occur at points outside the reactor 10 shown in FIG. 2. Nonetheless a discrete reactor is often desirable to allow for increased residence time, agitation and heating and/or cooling. When fixed bed catalyst is utilized, the reactor becomes the main location for the hydrogenation reaction to occur due to the presence of catalyst and is effect on the rate of hydrogenation. In preferred embodiments wherein reactor 10 is a fixed bed, reactor inlet stream 19 enters reactor 10 comprising catalyst, and hydrogenation of benzene occurs. In fixed bed reactor systems, the reactor 10 becomes the main location for the hydrogenation reaction to occur due to the presence of catalyst and is effect on the rate of hydrogenation. Reactants and catalyst may be first mixed in reactor 10. Reactor 10 may be charged with catalyst and if required, the catalyst is activated according to procedures recommended by the catalyst vendor(s).

Reaction heat may be removed from reactor 10 via any method known to one skilled in the art. The use of external heating and/or cooling heat transfer devices is also contemplated. Suitable locations for external heat transfer devices may be between the reactor 10 and the pump 5; between the pump 5 and the HSD 40; or between the HSD 40 and the reactor 10. There are many types of heat transfer devices that may be suitable and are known to those experienced in the art. Such exchangers might include shell and tube, plate, and coil heat exchangers.

Product stream 16 comprising cyclohexane and unconverted benzene, along with any byproducts (for example, hydrocracked products) may be extracted from HSS 100 via product stream 16. Upon removal from reactor 10, product stream 16 may be passed to a product recovery system (not shown) for further processing as known to those of skill in the art. The final cyclohexane product can, for example, be collected by separation means generally used in separating liquids such as distillation, centrifugation, density differences and chromatography. Unconverted benzene recovered via such downstream processing may be recycled via stream 20 to HSS 100. Additionally, excess hydrogen produced may be removed from or subsequent to reactor 10. This excess hydrogen stream is shown as stream 17. Excess hydrogen stream 17 may be re-circulated to high shear device inlet stream 13. Additionally, the excess hydrogen stream 17 maybe recycled to the pump 5 for pressurization prior to further mixing in HSD 40. Line 17 is connected to reactor 10 for removal of gas containing unreacted hydrogen, any other reaction gases and/or pressure. Line 17 may vent the head space of the reactor 10. Line 17 may comprise a compressor, or other device as known to one skilled in the art, to compress and transport gasses removed from the reactor 10. Additionally, line 17 functions to re-circulate gases to the high shear device 40. Recycling the unreacted gases from reactor 10 may serve to further accelerate the reactions.

In embodiments, use of the disclosed process comprising reactant mixing via external high shear mixer 40 allows use of lower temperature and/or pressure in reactor 10 than previously enabled. In embodiments, the high shear process provides a higher conversion of benzene to cyclohexane. In embodiments, the method comprises incorporating external high shear mixer 40 into an established process thereby reducing the operating temperature and/or pressure of the reaction in external high shear reactor 40 and/or enabling the increase in production (greater throughput) from a process operated without high shear mixer 40. In embodiments, reactor 10 is operated at near atmospheric pressure. In embodiments, for example, wherein a slurry of catalyst is circulated throughout HSS 100, reaction occurs within external high shear mixer 40; in such embodiments, reactor 10 may primarily serve to cool fluid, as much of the reaction occurs in external high shear mixer 40.

The process of the present invention should be conducted under conditions sufficient to promote the reduction of benzene and the impurities in the reactive mixture. It will be understood by those skilled in the art that conditions of temperature and pressure may vary depending on other variables such as the desired conversion, benzene concentration, hydrogen concentration, carbon monoxide concentration, catalyst particle size, catalyst composition, the heating/cooling efficiency of the reactor system, etc.

Potential benefits of this modified system include, but are not limited to, faster cycle times, increased throughput, reduced operating costs and/or reduced capital expense due to the possibility of designing smaller reactors and/or operating the reactor at lower temperature and/or pressure. In embodiments, the process of the present disclosure provides for a factor of more than about 5 times faster hydrogenation compared to hydrogenation in the absence of external high shear mixing. In embodiments, the process of the present disclosure provides for a factor of from about 5-10 times faster reaction rate compared to hydrogenation in the absence of external high shear mixing.

The application of enhanced mixing of the reactants by high shear device 40 potentially causes greater conversion of benzene to cyclohexane in some embodiments of the process. Further, the enhanced mixing of the reactants potentiates an increase in throughput of the process stream of the high shear system 100. In certain instances, the high shear device 40 is incorporated into an established process, thereby enabling an increase in production (i.e., greater throughput). Without wishing to be limited to a particular theory, it is believed that the level or degree of high shear mixing is sufficient to increase rates of mass transfer and also produces localized non-ideal conditions that enable the reactions to occur that would not otherwise be expected to occur based on Gibbs free energy predictions. The localized non ideal conditions are believed to occur within the high shear device resulting in increased temperatures and pressures with the most significant increase believed to be in localized pressures. The increase in pressures and temperatures within the high shear device are instantaneous and localized and quickly revert back to average system conditions once exiting the high shear device.

In embodiments, the method and system of this disclosure enable design of a smaller and/or less capital intensive process allowing selection of a reactor 10 having lower operating temperature and/or pressure capability than previously possible without the incorporation of external high shear mixer 40. In embodiments, the disclosed method reduces operating costs/increases production from an existing process. Alternatively, the disclosed method may reduce capital costs for the design of new processes.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A method for producing cyclohexane, comprising
    obtaining a high shear device having at least one rotor/stator set configured for producing a tip speed of at least 5 m/s;
    forming an emulsion of benzene and hydrogen gas, wherein said hydrogen gas comprises bubbles in the emulsion with a mean diameter of less than about 5 μm;
    introducing said emulsion into a reactor comprising a catalyst; and
    reacting liquid benzene with hydrogen gas in the presence of the solid catalyst at a temperature less than about 340° C.

2. The method of claim 1 wherein forming an emulsion comprises introducing benzene and hydrogen gas into the high shear device.

3. The method of claim 1 wherein said emulsion comprises hydrogen gas bubbles having an mean diameter of less than about 1.5 μm.

4. The method of claim 3 wherein the hydrogen gas bubbles have a mean diameter of less than about 100 nm.

5. The method of claim 1 wherein the high shear device is configured to have a nominal tip speed of greater than about 23 m/s.

6. The method of claim 1 wherein said high shear device is configured to produce a localized pressure of at least about 1000 MPa at the tip.

7. The method of claim 1 including subjecting said benzene and hydrogen gas bubbles to a shear rate of greater than about 20,000 $s^{-1}$.

8. The method of claim 1 wherein said high shear device is configured for an energy expenditure of at least 1000 $W/m^3$.

9. The method of claim 1 wherein said reactor is configured to maintain a pressure of at least about 250 psig.

10. The method of claim 9 wherein the reactor is configured to maintain a pressure between about 400 psig and about 800 psig.

11. The method of claim 1 wherein the hydrogen gas is reacted in the presence of the solid catalyst at a temperature of between about 190° C. and about 280° C.

12. The method of claim 11 wherein the catalyst comprises a metal selected from the group consisting of nickel, copper, chromium, manganese, iron, cobalt, zinc, molybdenum, tin, or combinations thereof.

13. The method of claim 1 further comprising injecting benzene and hydrogen in to the high shear device at a pressure of at least about 203 kPa.

14. A system for the production of cyclohexane from benzene the system comprising;
    at least one high shear device, configured for producing a dispersion of hydrogen gas bubbles in a benzene solution, the dispersion having an average bubble diameter of less than about 100 nm;
    at least one pump, configured for pressurizing a benzene solution positioned upstream of at least one high shear device, and in fluid communication with the at least one high shear device inlet; and
    a reactor comprising solid catalyst from which cyclohexane produced via reaction of hydrogen with benzene is extracted; the reactor fluidly connected to the outlet of the external high shear mixer.

15. The system of claim 14 wherein the high shear device comprises a high shear mill having a nominal tip speed of greater than about 23 m/s.

16. The system of claim 14 wherein said high shear device is configured to produce a localized pressure of at least about 1000 MPa at the tip.

17. The system of claim 14 wherein said high shear device is configured to produce a shear rate of greater than about 20,000 $s^{-1}$.

18. The system of claim 14 wherein said high shear device is configured for an energy expenditure of at least 1000 $W/m^3$.

19. The system of claim 14 wherein the pump is configured for injecting benzene and hydrogen into the high shear device at a pressure of at least about 203 kPa.

20. The system of claim 14 wherein said reactor is configured to maintain a pressure of at least about 250 psig.

21. The system of claim 20 wherein the reactor is configured to maintain a pressure between about 400 psig and about 800 psig.

22. The system of claim 14 wherein the reactor is configured to maintain a temperature of between about 190° C. and about 280° C.

23. The system of claim 22 further comprising at least one heat exchanger in thermal communication with the reactor.

24. The system of claim 14 wherein the catalyst comprises a metal selected from the group consisting of nickel, copper, chromium, manganese, iron, cobalt, zinc, molybdenum, tin, or combinations thereof.

* * * * *